United States Patent
Kesler et al.

(10) Patent No.: US 9,541,505 B2
(45) Date of Patent: *Jan. 10, 2017

(54) AUTOMATED POSTFLIGHT TROUBLESHOOTING SENSOR ARRAY

(75) Inventors: Paul Allen Kesler, Arlington, VA (US); Robert Daniel Kalinowski, Saint Charles, MO (US)

(73) Assignee: THE BOEING COMPANY, Chicago, IL (US)

( * ) Notice: Subject to any disclaimer, the term of this patent is extended or adjusted under 35 U.S.C. 154(b) by 18 days.

This patent is subject to a terminal disclaimer.

(21) Appl. No.: 12/701,033

(22) Filed: Feb. 5, 2010

(65) Prior Publication Data
US 2016/0153913 A1    Jun. 2, 2016

Related U.S. Application Data

(63) Continuation-in-part of application No. 12/372,616, filed on Feb. 17, 2009, now Pat. No. 9,418,496.

(51) Int. Cl.
*G06F 15/00* (2006.01)
*G01N 21/88* (2006.01)
(Continued)

(52) U.S. Cl.
CPC ............. *G01N 21/88* (2013.01); *G01N 21/01* (2013.01); *G01N 21/8806* (2013.01);
(Continued)

(58) Field of Classification Search
CPC ...... G07C 5/006; G07C 5/0808; G07C 5/0816; G07C 9/00111; G01N 21/00; G01N 21/8851; G01N 29/00; G01N 2291/00; G01N 2291/26; G01N 2291/2623; G01N 2291/2696; G01N 2291/2694; G01N 2291/106; G01N 2021/8854; G01N 2021/8858; G01N 21/88; G01N 21/01; G06F 17/00; G01M 5/00; G01M 5/0016; G01M 5/0033; G01M 5/0041; G01M 5/005; G01M 17/00; G01M 17/08; G06K 2017/0077

See application file for complete search history.

(56) References Cited

U.S. PATENT DOCUMENTS 2,849,701 A     8/1958  Clark
4,463,428 A     7/1984  Gilliam
(Continued)

FOREIGN PATENT DOCUMENTS

EP     0512866 A1    11/1992
EP     1193168 A2     4/2002
(Continued)

OTHER PUBLICATIONS

Merriam-Webster Dictionary, http://www.merriam-webster.com/dictionary/algorithm.*
(Continued)

*Primary Examiner* — Sujoy Kundu
*Assistant Examiner* — L. Anderson
(74) *Attorney, Agent, or Firm* — Yee & Associates, P.C.

(57) ABSTRACT

The advantageous embodiments provide an apparatus for identifying anomalies on an object comprising a sensor system and an analysis process. The sensor system is configured to detect a presence of the object, identify a speed of travel for the object, and determine a scan rate for the object using the speed of travel to generate scan results. The analysis process is configured to analyze the scan results and determine whether a number of maintenance anomalies are detected on the object using the scan results.

19 Claims, 7 Drawing Sheets

(51) Int. Cl.
*G01N 21/01* (2006.01)
*G07C 5/00* (2006.01)

(52) U.S. Cl.
CPC ......... *G01N 21/8851* (2013.01); *G07C 5/006* (2013.01); *G01N 2021/8854* (2013.01); *G01N 2291/106* (2013.01); *G01N 2291/26* (2013.01)

(56) References Cited

U.S. PATENT DOCUMENTS

| | | | |
|---|---|---|---|
| 4,827,416 A | 5/1989 | Kawagoe et al. | |
| 4,918,321 A | 4/1990 | Klenk et al. | |
| 5,014,042 A | 5/1991 | Michoud et al. | |
| 5,036,935 A | 8/1991 | Kohara | |
| 5,203,646 A | 4/1993 | Landsberger et al. | |
| 5,220,263 A | 6/1993 | Onishi et al. | |
| 5,237,404 A | 8/1993 | Tanaka et al. | |
| 5,318,254 A | 6/1994 | Shaw et al. | |
| 5,324,948 A | 6/1994 | Dudar et al. | |
| 5,334,982 A | 8/1994 | Owen | |
| 5,340,056 A | 8/1994 | Guelman et al. | |
| 5,351,621 A | 10/1994 | Tanaka et al. | |
| 5,416,476 A | 5/1995 | Rendon | |
| 5,487,440 A | 1/1996 | Seemann | |
| 5,490,646 A | 2/1996 | Shaw et al. | |
| 5,586,028 A | 12/1996 | Sekine et al. | |
| 5,633,707 A | 5/1997 | Seemann | |
| 5,726,705 A | 3/1998 | Imanishi et al. | |
| 5,831,570 A | 11/1998 | Ammar et al. | |
| 5,832,187 A | 11/1998 | Pedersen et al. | |
| 5,845,002 A | 12/1998 | Heck et al. | |
| 5,845,725 A | 12/1998 | Kawada | |
| 5,982,278 A | 11/1999 | Cuvelier | |
| 5,995,884 A | 11/1999 | Allen et al. | |
| 6,236,735 B1* | 5/2001 | Bjorner et al. | 382/101 |
| 6,266,138 B1 | 7/2001 | Keshavmurthy | |
| 6,293,141 B1 | 9/2001 | Nance | |
| 6,364,026 B1 | 4/2002 | Doshay | |
| 6,476,712 B1 | 11/2002 | Achterholt | |
| 6,565,361 B2 | 5/2003 | Jones et al. | |
| 6,606,563 B2 | 8/2003 | Corcoran, III | |
| 6,825,758 B1 | 11/2004 | Laitsaari | |
| 6,842,674 B2 | 1/2005 | Solomon | |
| 6,888,446 B2 | 5/2005 | Nantz et al. | |
| 6,898,484 B2 | 5/2005 | Lemelson et al. | |
| 6,904,335 B2 | 6/2005 | Solomon | |
| 6,907,799 B2 | 6/2005 | Jacobsen et al. | |
| 6,947,797 B2* | 9/2005 | Dean et al. | 700/79 |
| 6,953,094 B2 | 10/2005 | Ross et al. | |
| 6,970,576 B1 | 11/2005 | Tilsley | |
| 6,984,952 B2 | 1/2006 | Peless et al. | |
| 7,076,335 B2 | 7/2006 | Seemann | |
| 7,218,993 B2 | 5/2007 | Yasukawa et al. | |
| 7,236,861 B2 | 6/2007 | Paradis et al. | |
| 7,280,890 B2 | 10/2007 | Seemann | |
| 7,303,010 B2 | 12/2007 | de Guzman et al. | |
| 7,327,112 B1 | 2/2008 | Hlynka et al. | |
| 7,337,156 B2 | 2/2008 | Wippich | |
| 7,343,222 B2 | 3/2008 | Solomon | |
| 7,417,738 B2 | 8/2008 | Taylor et al. | |
| 7,499,772 B2 | 3/2009 | Wilcox et al. | |
| 7,501,616 B2 | 3/2009 | Wiklof | |
| 7,586,422 B2 | 9/2009 | Goodman et al. | |
| 7,626,513 B2 | 12/2009 | Goodman et al. | |
| 7,627,447 B2 | 12/2009 | Marsh et al. | |
| 7,714,702 B2 | 5/2010 | Khuzadi | |
| 7,765,038 B2 | 7/2010 | Appleby et al. | |
| 7,765,668 B2 | 8/2010 | Townsend et al. | |
| 7,796,018 B2 | 9/2010 | Khuzadi | |
| 7,797,095 B2 | 9/2010 | Rado | |
| 7,813,888 B2 | 10/2010 | Vian et al. | |
| 7,832,281 B2 | 11/2010 | Mian et al. | |
| 7,844,364 B2 | 11/2010 | McLurkin et al. | |
| 7,860,618 B2 | 12/2010 | Brandstetter et al. | |
| 7,894,948 B2 | 2/2011 | Stroud | |
| 7,896,113 B1 | 3/2011 | Ramirez | |
| 8,051,547 B2 | 11/2011 | Toh et al. | |
| 8,060,270 B2 | 11/2011 | Vian et al. | |
| 8,078,319 B2 | 12/2011 | Franke et al. | |
| 8,140,250 B2 | 3/2012 | Mian et al. | |
| 8,145,367 B2 | 3/2012 | Khatwa et al. | |
| 8,181,532 B2 | 5/2012 | Schmidt et al. | |
| 8,504,505 B2 | 8/2013 | Mintah | |
| 8,874,305 B2 | 10/2014 | Dolgov et al. | |
| 2002/0082769 A1 | 6/2002 | Church et al. | |
| 2003/0048081 A1 | 3/2003 | Seemann | |
| 2003/0089183 A1 | 5/2003 | Jacobsen et al. | |
| 2003/0125848 A1 | 7/2003 | Otake et al. | |
| 2003/0135327 A1 | 7/2003 | Levine et al. | |
| 2003/0169335 A1* | 9/2003 | Monroe | 348/143 |
| 2004/0030571 A1 | 2/2004 | Solomon | |
| 2004/0036630 A1 | 2/2004 | Jamieson et al. | |
| 2004/0054507 A1 | 3/2004 | Mott | |
| 2004/0055746 A1 | 3/2004 | Ross et al. | |
| 2004/0073324 A1* | 4/2004 | Pierro et al. | 700/90 |
| 2004/0073411 A1 | 4/2004 | Alston et al. | |
| 2004/0158358 A1 | 8/2004 | Anezaki et al. | |
| 2005/0033517 A1 | 2/2005 | Kondoh et al. | |
| 2005/0046569 A1 | 3/2005 | Spriggs et al. | |
| 2005/0073585 A1 | 4/2005 | Ettinger et al. | |
| 2005/0093687 A1 | 5/2005 | Katou | |
| 2005/0113943 A1 | 5/2005 | Nian | |
| 2005/0113975 A1 | 5/2005 | Seemann | |
| 2005/0126794 A1 | 6/2005 | Palmer et al. | |
| 2005/0217589 A1 | 10/2005 | Daniel et al. | |
| 2005/0251291 A1 | 11/2005 | Solomon | |
| 2005/0258943 A1 | 11/2005 | Mian et al. | |
| 2006/0085106 A1 | 4/2006 | Gaudiano et al. | |
| 2006/0114531 A1 | 6/2006 | Webb et al. | |
| 2006/0184291 A1 | 8/2006 | Paradis et al. | |
| 2006/0187014 A1 | 8/2006 | Li et al. | |
| 2006/0198952 A1 | 9/2006 | Nagase et al. | |
| 2006/0243857 A1 | 11/2006 | Rado | |
| 2006/0271251 A1 | 11/2006 | Hopkins | |
| 2007/0062299 A1 | 3/2007 | Mian et al. | |
| 2007/0081154 A1 | 4/2007 | Mapoles et al. | |
| 2007/0113690 A1 | 5/2007 | Wilcox et al. | |
| 2007/0129847 A1 | 6/2007 | Ulmer et al. | |
| 2007/0146728 A1 | 6/2007 | Pristner | |
| 2007/0203633 A1 | 8/2007 | Johnsen | |
| 2007/0208442 A1 | 9/2007 | Perrone | |
| 2007/0272841 A1 | 11/2007 | Wiklof | |
| 2008/0004749 A1 | 1/2008 | Hostettler | |
| 2008/0021604 A1 | 1/2008 | Bouvier et al. | |
| 2008/0140318 A1 | 6/2008 | Breed | |
| 2008/0143503 A1 | 6/2008 | Watabe et al. | |
| 2008/0148876 A1 | 6/2008 | Hock et al. | |
| 2008/0154458 A1 | 6/2008 | Brandstetter et al. | |
| 2008/0177411 A1 | 7/2008 | Marsh et al. | |
| 2008/0252489 A1 | 10/2008 | Naimer et al. | |
| 2008/0270866 A1 | 10/2008 | Choi et al. | |
| 2008/0297333 A1 | 12/2008 | Khuzadi | |
| 2008/0297375 A1 | 12/2008 | Khuzadi | |
| 2009/0055043 A1* | 2/2009 | Mian et al. | 701/29 |
| 2009/0079839 A1 | 3/2009 | Fischer et al. | |
| 2009/0219393 A1 | 9/2009 | Vian et al. | |
| 2009/0243828 A1 | 10/2009 | Hering et al. | |
| 2009/0285491 A1 | 11/2009 | Ravenscroft et al. | |
| 2009/0290757 A1* | 11/2009 | Mian et al. | 382/104 |
| 2010/0017052 A1 | 1/2010 | Luce | |
| 2010/0023201 A1 | 1/2010 | Kinney et al. | |
| 2010/0039294 A1 | 2/2010 | Feyereisen et al. | |
| 2010/0063650 A1 | 3/2010 | Vian et al. | |
| 2010/0094487 A1 | 4/2010 | Brinkman | |
| 2010/0211358 A1 | 8/2010 | Kesler et al. | |
| 2010/0235037 A1 | 9/2010 | Vian et al. | |
| 2010/0250022 A1 | 9/2010 | Hines et al. | |
| 2010/0271191 A1 | 10/2010 | de Graff et al. | |
| 2010/0312387 A1 | 12/2010 | Jang et al. | |
| 2010/0312388 A1 | 12/2010 | Jang et al. | |
| 2011/0313614 A1 | 12/2011 | Hinnant, Jr. et al. | |
| 2012/0038492 A1 | 2/2012 | Maggiore et al. | |
| 2012/0041639 A1 | 2/2012 | Followell et al. | |
| 2012/0081540 A1 | 4/2012 | Jang | |

(56) References Cited

U.S. PATENT DOCUMENTS

| | | |
|---|---|---|
| 2012/0130701 A1 | 5/2012 | Khella |
| 2013/0261876 A1 | 10/2013 | Froom et al. |
| 2014/0222325 A1 | 8/2014 | Followell et al. |

FOREIGN PATENT DOCUMENTS

| | | |
|---|---|---|
| EP | 1619625 | 1/2006 |
| EP | 1884453 A2 | 2/2008 |
| EP | 2208971 | 7/2010 |
| EP | 2259245 | 12/2010 |
| FR | 2930669 A1 | 10/2009 |
| GB | 2308656 | 7/1997 |
| GB | 2429819 | 3/2007 |
| JP | 2007183172 | 7/2007 |
| WO | WO2004081488 | 9/2004 |
| WO | WO2005113261 | 12/2005 |
| WO | WO2006053433 | 5/2006 |
| WO | WO2007080584 | 7/2007 |
| WO | 2008127468 A2 | 10/2008 |
| WO | 2009142933 A2 | 11/2009 |
| WO | WO2010141180 | 12/2010 |
| WO | WO2011119634 | 9/2011 |
| WO | WO2012021177 | 2/2012 |
| WO | WO2012021179 | 2/2012 |
| WO | WO2012047479 | 4/2012 |

OTHER PUBLICATIONS

Gunatilake et al., Image Understanding Algorithms for Remote Visual Inspection of Aircraft Surfaces, Carnegie Mellon University—Department of Electrical and Computer Engineering, Robotics Institute, School of Computer Science, 1997, entire document.*
Verma et al., Wavelet-Based Neural Net Application for Feature Detection and Classification, 2003, Journal Neural, Parallel and Scientific Computations—Advances in Intelligent Systems and Applications, vol. 11, entire document.*
PCT Search Report regarding Application PCT/US2011/029466, filing date Mar. 22, 2011, Issued by International Searching Authority.
"In-Sight Line Scan Vision System", Webinar, COGNEX, retrieved Feb. 5, 2010 http:www.cognex.com.
Frost, "A Practical Guide to Using the In-Sight 5604 Line Scan Vision System—Integration Note", Mar. 23, 2009, In-Sight Vision systems, COGNEX, pp. 1-20.
U.S. Appl. No. 11/857,217, filed Sep. 18, 2007, Vian et al.
U.S. Appl. No. 12/124,511, filed May 21, 2008, Vian et al.
U.S. Appl. No. 12/205,658, filed Sep. 5, 2008, Vian et al.
U.S. Appl. No. 12/124,565, filed May 21, 2008, Vian et al.
U.S. Appl. No. 12/479,667, filed Jun. 5, 2009, Jang et al.
U.S. Appl. No. 12/560,569, filed Feb. 5, 2010, Jang et al.
U.S. Appl. No. 12/404,493, filed Mar. 16, 2009, Vian et al.
GB Combined Search and Examination Report for application P49034GB/AER dated Jun. 10, 2010.
International Search Report for Application No. PCT/US2010/033917 dated Nov. 26, 2010.
"Unmanned Aerial Vehicle (UAV) ZALA 421-04M chosen for Aerial Monitoring of Forest Fires", published by news.wood.ru, Feb. 2010, 3 pages.
DeVault, "Robotic system for underwater inspection of bridge piers", IEEE Instrumentation & Measurement Magazine, vol. 3, Iss.3, Sep. 2000, pp. 32-37 (Abstract).
Gunatilake et al., "Image Understanding Algorithms for Remote Visual Inspection of Aircraft Surfaces", Proceedings of the SPIE conference on Machine Vision Applications in Industrial Inspection V, Copyright 1997, 12 pages.
Ollero, "Mutliple Heterogenous Unmanned Aerial Vehicles", Springer Tracts in Advanced Robotics, vol. 37, Copyright 2007, 233 pages (Abstract).

GB Search Report and Examination Report dated Jun. 14, 2011 regarding application GB1100763.0, applicant's reference P51280GB/AER/LJW, applicant The Boeing Company, 9 pages.
PCT Search Report and Written Opinion dated Jun. 8, 2011 regarding international application PCT/US2011/029766, applicant's reference 10-0173PCT, applicant The Boeing Company, 9 pages.
PCT Search Report dated Feb. 16, 2012 regarding international application PCT/US2011/030150, applicant's reference 10-0174PCT, applicant The Boeing Company, 6 pages.
PCT Search Report dated Feb. 7, 2012 regarding international application PCT/US2011/051830, applicant's reference 10-0602PCT, applicant The Boeing Company, 4 pages.
USPTO Office Action dated Apr. 13, 2012 regarding U.S. Appl. No. 12/404,493, 22 pages.
USPTO Office Action dated Jun. 15, 2012 regarding U.S. Appl. No. 13/086,521, 18 pages.
USPTO Office Action dated Nov. 8, 2010 regarding application U.S. Appl. No. 12/124,565, 13 pages.
USPTO Final Office Action dated Mar. 15, 2011 regarding U.S. Appl. No. 12/124,565, 14 pages.
USPTO Notice of Allowance dated Aug. 18, 2011 regarding U.S. Appl. No. 12/124,565, 7 pages.
USPTO Office Action dated Feb. 24, 2012 regarding U.S. Appl. No. 12/560,569, 27 pages.
USPTO Final Office Action dated Jul. 24, 2012 regarding U.S. Appl. No. 12/560,569, 23 pages.
USPTO Office Action dated May 10, 2011 regarding U.S. Appl. No. 12/372,616, 27 pages.
Response to Office Action dated Aug. 10, 2011 regarding U.S. Appl. No. 12/372,616, 21 pages.
USPTO Final Office Action dated Oct. 28, 2011 regarding U.S. Appl. No. 12/372,616, 30 pages.
Amendment submitted with RCE dated Jan. 30, 2012 regarding U.S. Appl. No. 12/372,616, 15 pages.
USPTO Office Action dated Feb. 15, 2012 regarding application 12/372,616, 22 pages.
Response to Office Action dated May 15, 2012 regarding U.S. Appl. No. 12/372,616, 16 pages.
USPTO Final Office Action dated Jul. 12, 2012 regarding U.S. Appl. No. 12/372,616, 23 pages.
USPTO Office Action dated Feb. 21, 2012 regarding U.S. Appl. No. 12/479,667, 25 pages.
Maggiore et al., "Runway Condition Monitoring", U.S. Appl. No. 12/730,594, filed Mar. 14, 2010, 43 pages.
Vian et al., "Fire Management System", U.S. Appl. No. 13/086,521, filed Apr. 14, 2011, 56 pages.
Final Office Action, dated Oct. 3, 2012, regarding U.S. Appl. No. 12/4004,493, 18 pages.
Office Action, dated Aug. 16, 2012, regarding U.S. Appl. No. 12/730,594, 25 pages.
Office Action, dated Aug. 31, 2012, regarding U.S. Appl. No. 12/854,646, 19 pages.
Office Action, dated Dec. 21, 2012, regarding U.S. Appl. No. 12/372,616, 39 pages.
Final Office Action, dated Dec. 20, 2012, regarding U.S. Appl. No. 12/730,594, 35 pages.
Office Action, dated Dec. 6, 2012, regarding U.S. Appl. No. 12/897,158, 51 pages.
Office Action, dated May 23, 2013, regarding U.S. Appl. No. 12/70,594, 28 pages.
Final Office Action, dated Mar. 7, 2013, regarding U.S. Appl. No. 12/854,646, 22 pages.
Office Action, dated Mar. 28, 2013, regarding U.S. Appl. No. 12/854,671, 37 pages.
Office Action, dated Sep. 10, 2013, regarding U.S. Appl. No. 12/372,616, 25 pages.
Office Action, dated Jul. 18, 2013, regarding U.S. Appl. No. 12/404,493, 42 pages.
Office Action, dated Aug. 28, 2013, regarding U.S. Appl. No. 12/560,569, 46 pages.
Notice of Allowance, dated Jul. 31, 2013, regarding U.S. Appl. No. 12/854,646, 19 pages.

(56) References Cited

OTHER PUBLICATIONS

Final Office Action, dated Jul. 12, 2013, regarding U.S. Appl. No. 12/854,671, 17 pages.
Final Office Action, dated Jun. 26, 2013, regarding U.S. Appl. No. 12/897,158 38 pages.
European Patent Office Communication, dated Jul. 23, 2013, regarding Application No. EP11713911.3, 6 pages.
Final Office Action, dated Dec. 10, 2013, regarding U.S. Appl. No. 12/730,594, 33 pages.
Notice of Allowance, dated Apr. 9, 2014, regarding U.S. Appl. No. 12/404,493, 10 pages.
Final Office Action, dated Apr. 2, 2014, regarding U.S. Appl. No. 12/372,616, 24 pages.
Final Office Action, dated Feb. 28, 2014, regarding U.S. Appl. No. 12/560,569, 43 pages.
Notice of Allowance, dated Feb. 27, 2014, regarding U.S. Appl. No. 12/730,594, 11 pages.
Office Action, dated Apr. 8, 2014, regarding U.S. Appl. No. 12/897,158, 33 pages.
Final Office Action, dated Feb. 19, 2014, regarding U.S. Appl. No. 13/086,521, 18 pages.
Office Action, dated Sep. 16, 2014, regarding U.S. Appl. No. 12/560,569, 46 pages.
Office Action, dated Aug. 8, 2014, regarding U.S. Appl. No. 13/086,521, 20 pages.
Final Office Action, dated Sep. 8, 2014, regarding U.S. Appl. No. 12/897,158 36 pages.
Final Office Action, dated Jan. 14, 2015, regarding U.S. Appl. No. 13/086,521, 23 pages.
Final Office Action, dated Dec. 29, 2014, regarding U.S. Appl. No. 12/560,569, 17 pages.
Notice of Allowance, dated Oct. 28, 2014, regarding U.S. Appl. No. 12/897,158, 12 pages.
Notice of allowance, dated Jan. 28, 2015, regarding U.S. Appl. No. 12/560,569, 6 pages.
Office Action, dated Sep. 16, 2015, regarding U.S. Appl. No. 12/372,616, 23 pages.
Office Action, dated Oct. 7, 2015, regarding U.S. Appl. No. 14/246,143, 55 pages.
Notice of Allowance, dated Apr. 7, 2016, regarding U.S. Appl. No. 12/372,616, 14 pages.
Final Office Action, dated Feb. 23, 2016, regarding U.S. Appl. No. 14/246,143, 20 pages.
European Patent Office Communication, dated Mar. 3, 2016, regarding Application No. 11714174.7, 5 pages.

\* cited by examiner

AUTOMATED POSTFLIGHT TROUBLESHOOTING SENSOR ARRAY

The present invention is a continuation-in-part (CIP) of and claims priority to the following patent application: entitled "Automated Postflight Troubleshooting," Ser. No. 12/372,616, filed Feb. 17, 2009, and is incorporated herein by reference.

BACKGROUND INFORMATION

1. Field

The present disclosure relates to a maintenance system and, in particular, to a method and apparatus for maintenance planning for products. Still more particularly, the present disclosure relates to a method, apparatus, and computer usable program code for identifying external maintenance discrepancies.

2. Background

In planning for maintenance of products, a number of different processes may be present. When the product is an aircraft, for example, computer based maintenance planning tools may aid in the planning process by integrating regulatory requirements with emerging maintenance needs to help calculate the time required to perform the many tasks necessary to keep the aircraft in airworthy condition and compliant with federal regulations.

Time for conducting post-flight maintenance is lost between the time an aircraft lands and the time the aircraft reaches the ramp from the runway. Increased turn around time due to maintenance requirements is more likely as the maintenance inspection time is lost while an aircraft is taxiing. Visual health inspections are time consuming and human endurance for lengthy, repetitive inspections induces failure rates for detecting anomalies. The human eye is also limited in spectrum and may have difficulty seeing certain types of fluid leaks.

Accordingly, it would be advantageous to have a method and apparatus which takes into account one or more of the issues discussed above as well as possibly other issues.

SUMMARY

The different advantageous embodiments provide an apparatus for identifying anomalies on an object comprising a sensor system and an analysis process. The sensor system is configured to detect a presence of the object, identify a speed of travel for the object, and determine a scan rate for the object using the speed of travel to generate scan results. The analysis process is configured to analyze the scan results and determine whether a number of maintenance anomalies are detected on the object using the scan results.

The different advantageous embodiments further provide a method for identifying a scan rate for an object. A presence of the object approaching a control area is detected using a sensor system. An array encoder is activated to detect a speed of travel for the object. The speed of travel for the object is monitored to determine a scan rate.

The different advantageous embodiments further provide a method for identifying anomalies on an object. A presence of the object is detected in a control area using a sensor system. In response to detecting the presence of the object, a speed of travel for the object is monitored. A scan rate for the object is identified using the speed of travel for the object. The object is scanned using the scan rate identified to form scan results. The scan results are analyzed. A determination is made as to whether a number of maintenance anomalies are detected on the object using the scan results.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
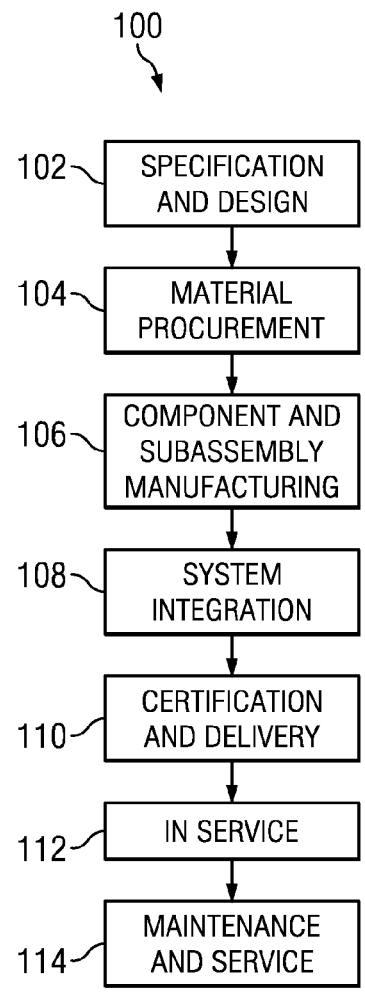
FIG. 1 is an illustration of an aircraft manufacturing and service method in which an advantageous embodiment may be implemented.
Figure 2:
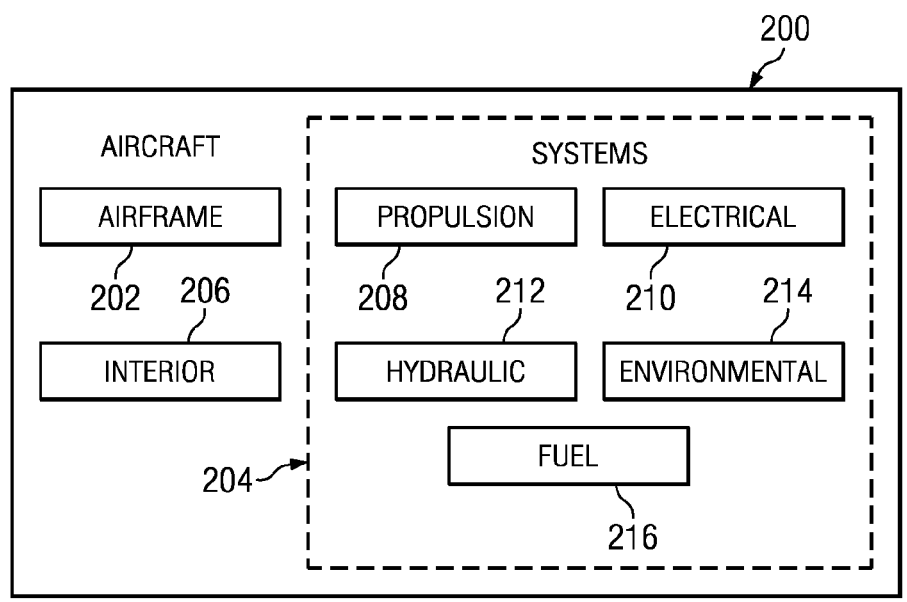
FIG. 2 is an illustration of an aircraft in which an advantageous embodiment may be implemented.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and majorsystem subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, environmental system 214, and fuel system 216. Any number of other systems may be included. Although an aerospace example is shown, different advantageous embodiments may be applied to other industries, such as the automotive industry.

Apparatus and methods embodied herein may be employed during at least one of the stages of aircraft manufacturing and service method 100 in FIG. 1. For example, external maintenance anomalies identified during certification and delivery 110 in FIG. 1 may be addressed while aircraft 200 is in maintenance and service 114 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments may substantially expedite the assembly of and/or reduce the cost of aircraft 200.

The different advantageous embodiments recognize and take into account that currently used systems for conducting post-flight maintenance lose the time from when an aircraft lands until it reaches the ramp from the runway, which increases the potential turn around time due to maintenance requirements that may not be identified until the aircraft has finished taxiing. The different advantageous embodiments recognize that initial maintenance inspection time is lost while an aircraft is taxiing.

The different advantageous embodiments recognize and take into account that currently used systems for identifying external maintenance anomalies for an aircraft, for example, rely upon human inspection at the airport gate or maintenance area. The different advantageous embodiments recognize that the locations at which inspection for external maintenance anomalies can take place is limited. The different advantageous embodiments also recognize that currently used systems may cope with this problem by utilizing maintenance datalinks, which have the ability to detect some structural health issues but lack any ability to autonomously detect latent surface anomalies, such as cracks or dents for example.

The different advantageous embodiments also recognize and take into account that maintenance datalinks are expensive and have bandwidth limitations that significantly restrict the amount of information that can be transmitted. The different advantageous embodiments recognize that this leads to many companies choosing not to use maintenance datalinks at all, and relying solely on inspections that take place after the aircraft has finished taxiing.

Thus, one or more of the different advantageous embodiments provide an apparatus for identifying anomalies on an object comprising a sensor system and an analysis process. The sensor system is configured to detect a presence of the object, identify a speed of travel for the object, and determine a scan rate for the object using the speed of travel to generate scan results. The analysis process is configured to analyze the scan results and determine whether a number of maintenance anomalies are detected on the object using the scan results.

The different advantageous embodiments further provide a method for identifying a scan rate for an object. A presence of the object approaching a control area is detected using a sensor system. An array encoder is activated to detect a speed of travel for the object. The speed of travel for the object is monitored to determine a scan rate.

The different advantageous embodiments further provide a method for identifying anomalies on an object. A presence of the object is detected in a control area using a sensor system. In response to detecting the presence of the object, a speed of travel for the object is monitored. A scan rate for the object is identified using the speed of travel for the object. The object is scanned using the scan rate identified to form scan results. The scan results are analyzed. A determination is made as to whether a number of maintenance anomalies are detected on the object using the scan results.

Figure 3:
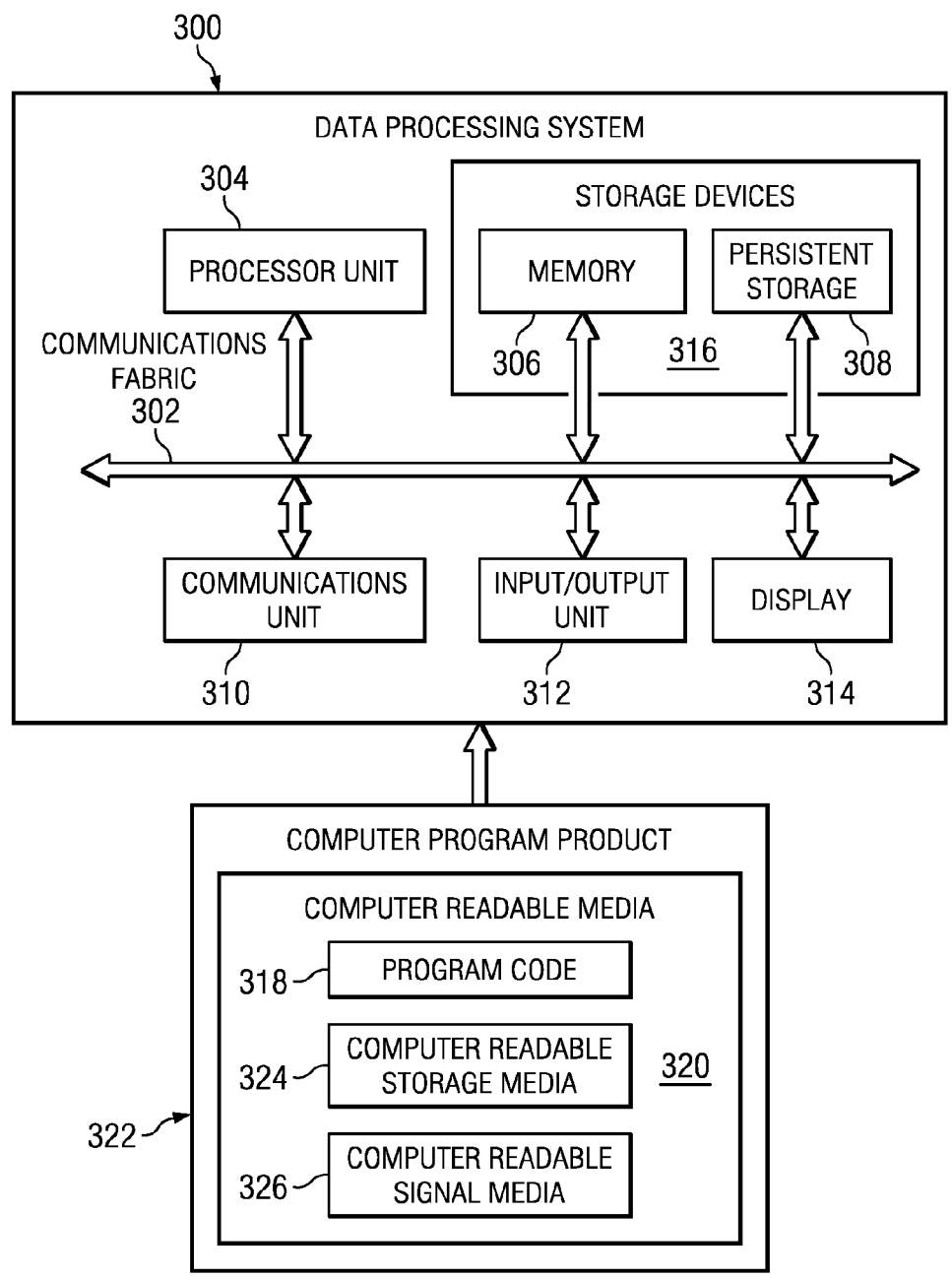
FIG. 3 is an illustration of a data processing system in accordance with an advantageous embodiment.

Turning now to FIG. 3, an illustration of a data processing system is depicted in accordance with an illustrative embodiment. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems, in which a main processor is present with secondary processors on a single chip. As another illustrative example, processor unit 304 may be a symmetric multi-processor system containing multiple processors of the same type.

Memory 306 and persistent storage 308 are examples of storage devices 316. A storage device is any piece of hardware that is capable of storing information, such as, for example, without limitation, data, program code in functional form, and/or other suitable information either on a temporary basis and/or a permanent basis. Memory 306, in these examples, may be, for example, a random access memory, or any other suitable volatile or non-volatile storage device. Persistent storage 308 may take various forms, depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 may be removable. For example, a removable hard drive may be used for persistent storage 308.

Communications unit 310, in these examples, provides for communication with other data processing systems or devices. In these examples, communications unit 310 is a network interface card. Communications unit 310 may provide communications through the use of either or both physical and wireless communications links.

Input/output unit 312 allows for the input and output of data with other devices that may be connected to data processing system 300. For example, input/output unit 312 may provide a connection for user input through a keyboard, a mouse, and/or some other suitable input device. Further, input/output unit 312 may send output to a printer. Display 314 provides a mechanism to display information to a user.

Instructions for the operating system, applications, and/or programs may be located in storage devices 316, which are in communication with processor unit 304 through communications fabric 302. In these illustrative examples, the instructions are in a functional form on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code, in the different embodiments, may be embodied on different physical or computer readable storage media, such as memory 306 or persistent storage 308.

Program code 318 is located in a functional form on computer readable media 320 that is selectively removable and may be loaded onto or transferred to data processing system 300 for execution by processor unit 304. Program code 318 and computer readable media 320 form computer program product 322. In one example, computer readable media 320 may be computer readable storage media 324 or computer readable signal media 326. Computer readable storage media 324 may include, for example, an optical or magnetic disc that is inserted or placed into a drive or other device that is part of persistent storage 308 for transfer onto a storage device, such as a hard drive, that is part of persistent storage 308. Computer readable storage media 324 also may take the form of a persistent storage, such as a hard drive, a thumb drive, or a flash memory that is connected to data processing system 300. In some instances, computer readable storage media 324 may not be removable from data processing system 300.

Alternatively, program code 318 may be transferred to data processing system 300 using computer readable signal media 326. Computer readable signal media 326 may be, for example, a propagated data signal containing program code 318. For example, computer readable signal media 326 may be an electromagnetic signal, an optical signal, and/or any other suitable type of signal. These signals may be transmitted over communications links, such as wireless communications links, an optical fiber cable, a coaxial cable, a wire, and/or any other suitable type of communications link. In other words, the communications link and/or the connection may be physical or wireless in the illustrative examples.

In some illustrative embodiments, program code 318 may be downloaded over a network to persistent storage 308 from another device or data processing system through computer readable signal media 326 for use within data processing system 300. For instance, program code stored in a computer readable storage media in a server data processing system may be downloaded over a network from the server to data processing system 300. The data processing system providing program code 318 may be a server computer, a client computer, or some other device capable of storing and transmitting program code 318.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown. The different embodiments may be implemented using any hardware device or system capable of executing program code. As one example, data processing system 300 may include organic components integrated with inorganic components and/or may be comprised entirely of organic components excluding a human being. For example, a storage device may be comprised of an organic semiconductor.

As another example, a storage device in data processing system 300 is any hardware apparatus that may store data. Memory 306, persistent storage 308, and computer readable media 320 are examples of storage devices in a tangible form.

In another example, a bus system may be used to implement communications fabric 302 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 306 or a cache such as found in an interface and memory controller hub that may be present in communications fabric 302.

Figure 4:
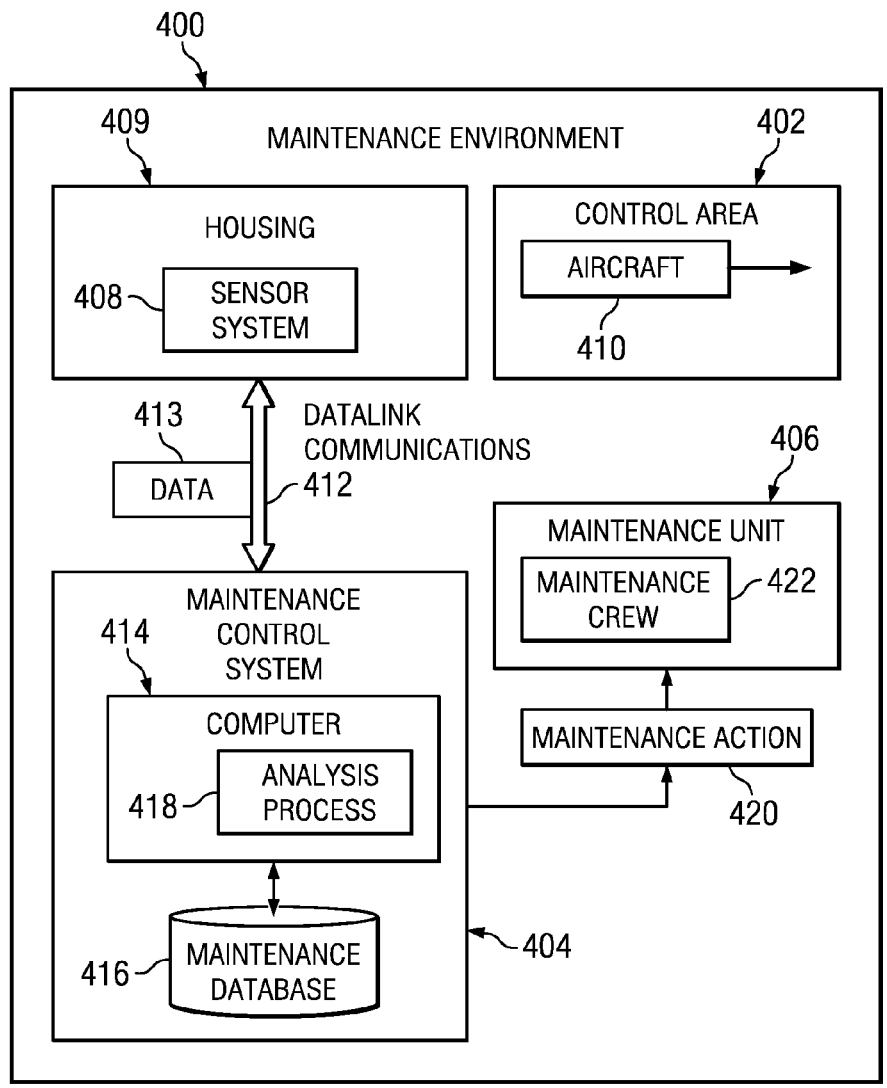
FIG. 4 is an illustration of a maintenance environment in accordance with an advantageous embodiment.

Turning now to FIG. 4, an illustration of a maintenance environment is depicted in accordance with an advantageous embodiment. Maintenance environment 400 may be implemented during aircraft manufacturing and service method 100 as shown in FIG. 1. For example, maintenance environment 400 may be implemented during in service 112 and/or maintenance and service 114 in FIG. 1.

Maintenance environment 400 includes control area 402, maintenance control system 404, maintenance unit 406, and sensor system 408. Control area 402 is any location and/or area in which an object may be scanned and/or inspected. Control area 402 may be, for example, without limitation, a taxiway, runway, paved surface, a portion of a taxiway, a portion of a runway, a portion of a paved surface, and/or any area or location in which an object may be scanned. In one advantageous embodiment, control area 402 may be a checkpoint of object traffic moving throughout a larger environment, for example. Control area 402 may include sensor system 408. Aircraft 410 moves through control area 402 in this example.

Sensor system 408 may be implemented within housing 409 in one advantageous embodiment. Housing 409 may be, for example, without limitation, a weather resistant housing. Sensor system 408 may be implemented as a number of sensor systems within and/or adjacent to control area 402. As used herein, a number refers to one or more sensor systems. Sensor system 408 may be distributed on a number of sides of control area 402. For example, in one advantageous embodiment, sensor system 408 may be distributed on either side of a runway or a taxiway. In another advantageous embodiment, sensor system 408 may be distributed at either end of a runway or a taxiway. In yet another advantageous embodiment, sensor system 408 may be distributed horizontally across a runway or taxiway, as depicted in more detail in FIG. 5. In yet another advantageous embodiment, sensor system 408 may be distributed vertically on either side of a runway or taxiway, as depicted in more detail in FIG. 5.

Aircraft 410 is an example of an object moving through control area 402. Aircraft 410 may be one example of aircraft 200 in FIG. 2. Sensor system 408 detects aircraft 410 as aircraft 410 approaches control area 402. Sensor system 408 scans aircraft 410 as aircraft 410 moves through control area 402. Sensor system 408 may detect maintenance anomalies on aircraft 410, such as, for example, without limitation, cracks, dents, depressions, bulges, buckling, warping, drips, leaks, corrosion, rust, open/missing access panels, and/or other anomalies. A maintenance anomaly is any type of anomaly that requires maintenance. The anomaly may be inside the object, on an exterior surface of the object, on an interior surface of the object, within a structure of the object, and/or any other suitable area of the object.

Sensor system 408 communicates with maintenance control system 404 using datalink communications 412. Datalink communications 412 may use a medium that is, for example without limitation, physical and/or wireless. Datalink communications 412 also may be part of a network. Sensor system 408 may transmit scan results in the form of data 413 over datalink communications 412 to maintenance control system 404.

In this illustrative example, maintenance control system 404 includes computer 414 and maintenance database 416. Computer 414 may be any type of data processing system, such as data processing system 300 in FIG. 3. Computer 414 includes analysis process 418. Analysis process 418 interacts with maintenance database 416 to identify maintenance anomalies using scan results from sensor system 408. Analysis process 418 may generate maintenance action 420 and transmit maintenance action 420 to maintenance unit 406. Maintenance action 420 may be, for example, a repair, an adjustment, a replacement of a part, no action required, and/or some other suitable action. Maintenance crew 422 of maintenance unit 406 may receive maintenance action 420 from analysis process 418 and execute maintenance action 420 on aircraft 410.

The illustration of maintenance environment 400 in FIG. 4 is not meant to imply physical or architectural limitations on the manner in which different advantageous embodiments may be implemented. Other components in addition or in place of the ones illustrated may be used. Some components may be unnecessary in some advantageous embodiments. Also, the blocks are presented to illustrate some functional components and combined and/or divided into different blocks when implemented in hardware and/or software.

For example, in some advantageous embodiments, analysis process 418 could be implemented within sensor system 408. In this illustrative example, maintenance action 420 may be transmitted directly from analysis process 418 implemented in sensor system 408 to maintenance unit 406, while simultaneously being transmitted for storage to maintenance database 416 at a remote location. Also, maintenance database 416 may be located at the same data processing system or distributed over many data processing systems.

As another example, additional sensor systems in addition to sensor system 408 maybe used in control area 402 to scan other aircraft in addition to aircraft 410. Also, maintenance environment 400 also may have additional control areas in addition to control area 402. In other advantageous embodiments, data 413 transmitted by sensor system 408 over datalink communications 412 may pass through intermediate nodes before being received by maintenance control system 404.

Figure 5:
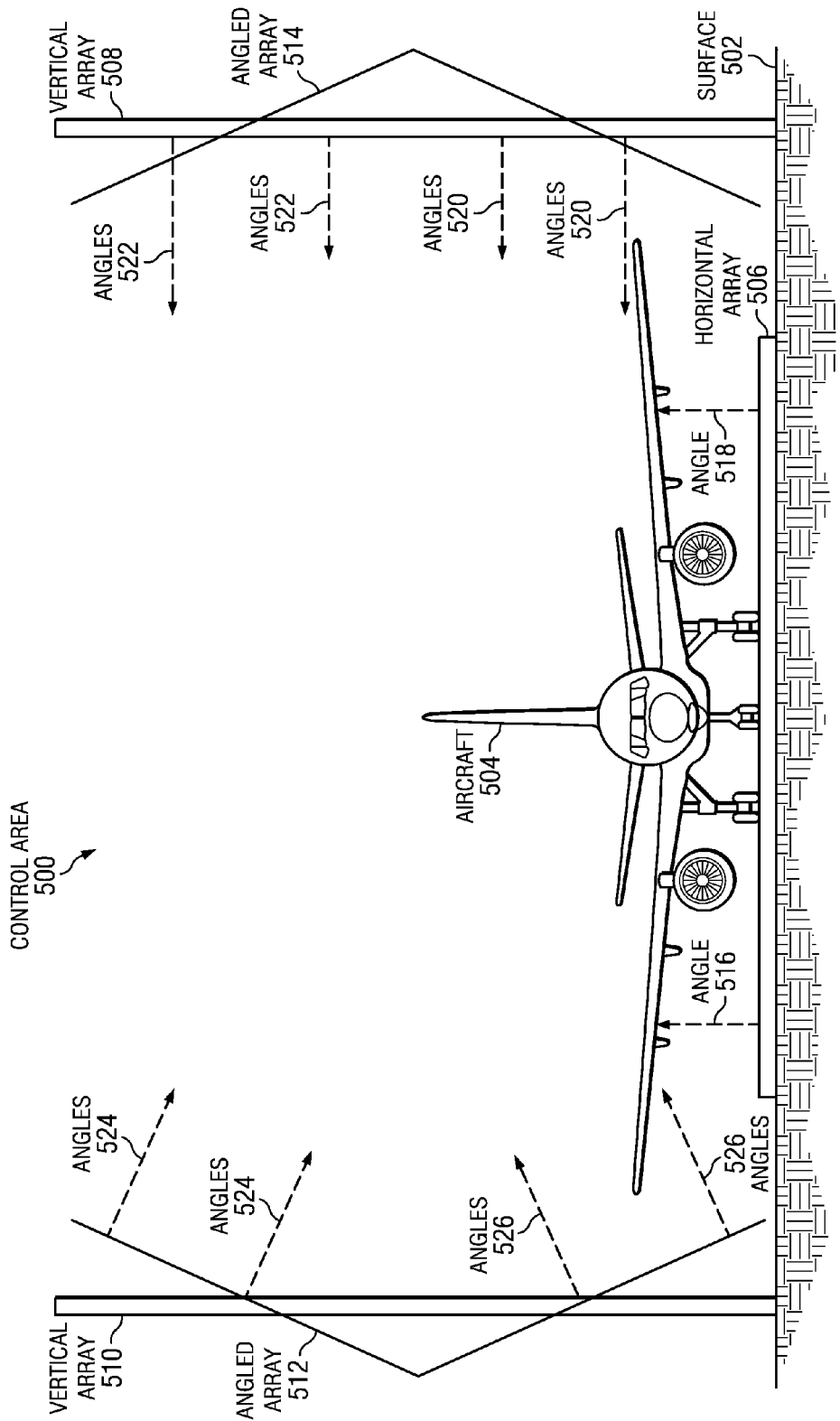
FIG. 5 is an illustration of a control area in accordance with an advantageous embodiment.

With reference now to FIG. 5, an illustration of a control area is provided in which advantageous embodiments may be implemented. Control area 500 is an illustrative example of one implementation of control area 402 in FIG. 4.

Control area 500 may be, for example, without limitation, a taxiway or runway having surface 502. Aircraft 504 may travel along surface 502. Control area 500 may include a number of sensor systems with a number of sensor arrays, such as sensor system 408 in FIG. 4, for example. A sensor array is any configuration of a number of sensor components.

In this illustrative example, control area 500 includes horizontal array 506, vertical array 508, vertical array 510, angled array 512, and angled array 514. Horizontal array 506 is located adjacent to and horizontal to surface 502 of control area 500. Horizontal array 506 may be embedded and span the width of surface 502 and/or control area 500 at a given point, such as the width of a runway at a specific location of the runway, for example.

Vertical array 508 and vertical array 510 are each located adjacent to and vertical to surface 502 of control area 500. Vertical array 508 and vertical array 510 may be located on either side of control area 500, such as on either side of a taxiway or runway, for example. Angled array 512 and angled array 514 are located similarly to vertical array 508 and vertical array 510, in this illustrative example, both adjacent to and vertical to surface 502 of control area 500. An angled array may span a vertical distance relative to the surface, such as surface 502, in an angular configuration, as depicted by angled array 512 and angled array 514. The angle of angled array 512 and angled array 514 relative to surface 502 may be, for example, without limitation, 170°, 160°, 150°, 140°, and/or any other suitable degree of angle that is less than 180°.

Each portion of an array may provide a different scan angle for a number of sensor systems associated with the array. Horizontal array 506 may provide angle 516 and angle 518, for example. Angle 516 and angle 518 are illustrative examples of a scan angle that may capture images and/or scans of the underside of aircraft 504 as aircraft 504 passes over horizontal array 506 within control area 500.

Vertical array 508 and vertical array 510 provide similar scan angles, where vertical array 510 may provide angles that mirror angles provided by vertical array 508, for example. In this illustrative example, vertical array 508 may provide angles 520 and angles 522. Angles 520 and angles 522 are illustrative examples of a number of scan angles that may capture images and/or scans of a side of aircraft 504 as aircraft 504 passes alongside vertical array 508 within control area 500.

Angled array 512 and angled array 514 provide similar scan angles, where angled array 512 may provide angles that mirror angles provided by angled array 514, for example. In this illustrative example, angled array 512 may provide angles 524 and angles 526. Angles 524 and angles 526 are illustrative examples of a number of scan angles that may capture images and/or scans of a top, bottom, and/or side of aircraft 504 as aircraft 504 passes alongside angled array 512 within control area 500.

The illustration of control area 500 in FIG. 5 is not meant to imply physical or architectural limitations on the manner in which different advantageous embodiments may be implemented. Other components in addition or in place of the ones illustrated may be used. Some components may be unnecessary in some advantageous embodiments. Also, the blocks are presented to illustrate some functional components and combined and/or divided into different blocks when implemented in hardware and/or software.

For example, in some advantageous embodiments, only one type of array may be implemented, such as one of horizontal array 506, vertical arrays 508 and 510, and/or angled arrays 512 and 514. In other advantageous embodiments, control area 500 may be implemented with any combination of any number of types of arrays. In yet other advantageous embodiments, arrays may be implemented in any number of shapes and/or configurations.

In other advantageous embodiments, angled array 512 and angled array 514 may be implemented in two or more portions positioned relative to each other but not attached to each other. For example, angled array 512 may be implemented with an upper portion providing scan angles 524 and a lower portion providing scan angles 526. In this illustrative example, the upper portion and lower portion may be separate from each other, and positioned relative to each other in order to capture a certain number of scan angles and/or degree of scan.

Figure 6:
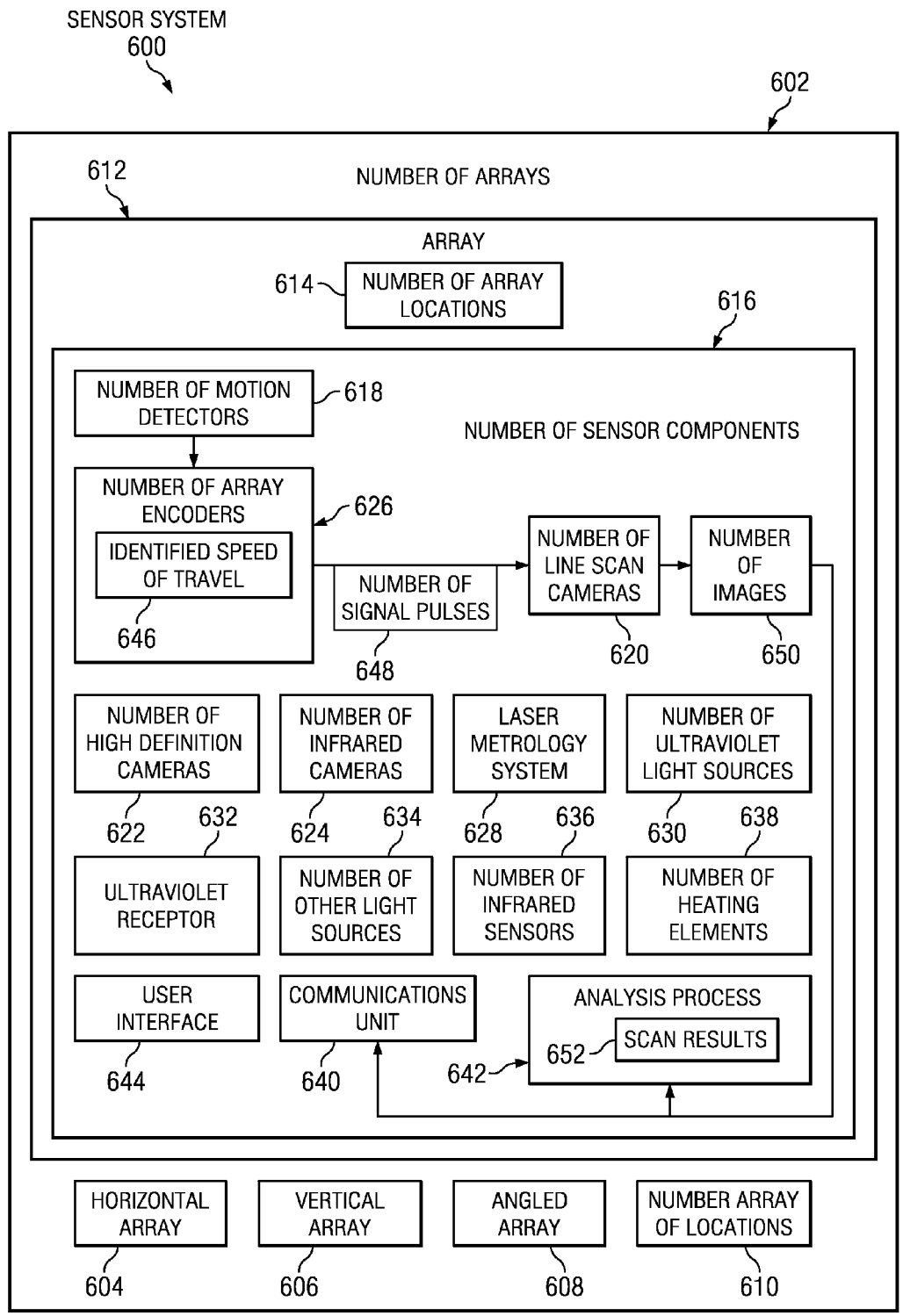
FIG. 6 is an illustration of a sensor system in accordance with an advantageous embodiment.

With reference now to FIG. 6, a diagram of a sensor system is depicted in accordance with an advantageous embodiment. Sensor system 600 may be used with or implemented as part of a data processing system, such as data processing system 300 in FIG. 3. Sensor system 600 is an example of one implementation of sensor system 408 in FIG. 4.

Sensor system 600 is a system with a number of sensors and may be a number of sensor systems used to collect information about an object moving towards and/or through an environment. A number as used herein refers to one or more items. For example, a number of sensors is one or more sensors, and a number of sensor systems is one or more sensor systems.

In one advantageous embodiment, sensor system 600 includes number of arrays 602. Number of arrays 602 may be any type of configuration of sensor components. Number of arrays 602 may be configured in a number of different types of configurations including, but not limited to, horizontal array 604, vertical array 606, and angled array 608. Each array in number of arrays 602 includes number of array locations 610. Number of array locations 610 is any location along an array configuration associated with a sensor component.

Array 612 is an illustrative example of number of arrays 602. Array 612 includes number of array locations 614 and number of sensor components 616. Number of sensor components 616 may be associated with number of array locations 614 of array 612, in this illustrative example.

Number of sensor components 616 includes number of motion detectors 618, number of line scan cameras 620, number of high definition cameras 622, number of infrared cameras 624, number of array encoders 626, laser metrology system 628, number of ultraviolet light sources 630, ultraviolet receptor 632, number of other light sources 634, number of infrared sensors 636, number of heating elements 638, communications unit 640, analysis process 642, and user interface 644.

Number of motion detectors 618 is any device that contains a physical mechanism or electronic sensor that is capable of detecting motion. Number of motion detectors 618 may detect the presence of a moving object approaching a control area, adjacent to a control area, and/or within a control area, such as control area 402 in FIG. 4. In one advantageous embodiment, number of motion detectors 618 is integrated with or connected to other components of sensor system 600 in order to activate other components, such as number of array encoders 626, for example, to the presence of a moving object within range. When number of motion detectors 618 is triggered by a moving object, such as aircraft 410 in FIG. 4, number of motion detectors 618 may send a signal to number of array encoders 626 to activate number of array encoders 626, for example. In another advantageous embodiment, number of motion detectors 618 may be configured to send a signal to analysis process 642 when the presence of a moving object is detected.

Number of line scan cameras 620 use line scan technology to build an image from a moving object as the object moves past the cameras.

Number of high definition cameras 622 may be a number of standard still-image cameras, which may be used alone for color information or with additional cameras to generate stereoscopic, or three-dimensional, images. Number of infrared cameras 624 may form an image using infrared radiation. When number of high definition cameras 622 is used along with additional cameras to generate stereoscopic images, the cameras may be set with different exposure settings to provide improved performance over a range of lighting conditions. Number of high definition cameras 622 may also be a video camera that captures and records moving images, in one advantageous embodiment.

Number of array encoders 626 measures speed of travel for an object, such as aircraft 410 in FIG. 4, using non-contact speed measurement devices. Number of array encoders 626 may use devices such as, for example, without limitation, a laser Doppler velocimeter (LDV), a laser surface velocimeter (LSV), and/or any other suitable speed measurement device.

Number of array encoders 626 measures a speed of travel for an object to form identified speed of travel 646. Number of array encoders 626 then converts identified speed of travel 646 into number of signal pulses 648 and transmits number of signal pulses 648 to number of line scan cameras 620. Number of line scan cameras 620 require a known speed of an object in order to build an image of an object moving past the cameras. Number of line scan cameras 620 use number of signal pulses 648 to identify a scan rate for the object moving past array 612. A scan rate may refer to the number of electrical signal pulses sent to a number of cameras to cause the number of cameras to take an exposure of the object on each signal pulse. The number of electrical signal pulses may be sent at varying rates depending upon the speed of an object detected, for example.

Laser metrology system 628 is any scanning laser metrology system that uses laser beams to measure a surface. Laser metrology system 628 scans a surface and creates a three-dimensional map, which can be used to measure anomalies, such as, for example, without limitation, cracks, dents, and the like. Laser metrology system 628 may be configured to measure a surface, such as aircraft 410 in FIG. 4 moving through control area 402 for example.

Number of ultraviolet light sources 630 emits ultraviolet light. Ultraviolet light is electromagnetic radiation with a wavelength shorter than that of visible light. Ultraviolet light may be used to detect anomalies such as, for example, fluid leaks that are difficult to identify in a visible light spectrum. Ultraviolet receptor 632 receives the bounce-back of ultraviolet light wavelengths when number of ultraviolet light sources 630 emits ultraviolet light. Ultraviolet receptor 632 transforms the bounce-back wavelengths into a visible light spectrum viewable by a human eye. One advantageous embodiment of ultraviolet receptor 632 may be a digital camera using ultraviolet light filters. This digital camera may capture images of an object illuminated by number of ultraviolet light sources 630 in an ultraviolet light range, in one illustrative example.

Number of other light sources 634 may be included in array 612 to enhance surface illumination of a control area, such as control area 402 in FIG. 4, for example. Number of other light sources 634 may include, for example, without limitation, incandescent light sources, thermal light sources, light-emitting diodes, fluorescent light sources, and/or any other suitable light source.

Number of infrared sensors 636 detects differences in ambient temperature. Number of infrared sensors 636 may be used to detect anomalies such as, for example, fluid leaks that are difficult to identify in a visible light spectrum. Number of infrared sensors 636 is capable of detecting fluid leaks or streaks because the fluid may be a different temperature than the immediate surrounding surface of the object. The difference in temperature may reveal the fluid as a different temperature gradient shade in the infrared scan. In another advantageous embodiment, infrared scans may show hot spots on the surface of an object that should not normally be there as compared to an as designed infrared scan of the object. These hot spots can be indicative of anomalies on or below the surface of the object. For example, a hot spot below a mid-wing surface of an aircraft that corresponds to the position of a fuel pump beneath the wing surface may be indicative of the fuel pump overheating and/or being on the verge of failure.

Number of heating elements 638 may be included in array 612 to keep number of sensor components 616 at a desired operating temperature range. Number of heating elements 638 may include, for example, without limitation tubular heaters, flange heaters, boiler heaters, screw plug heaters, circulation heaters, strip heaters, cartridge heaters, band heaters, and/or any other suitable heating element.

Communications unit 640, in these examples, provides for communications with other data processing systems or devices. In one advantageous embodiment, communications unit 640 may be a network interface card. Communications unit 640 may provide communications through the use of either or both physical and wireless communications links.

In an advantageous embodiment, sensor system 600 detects a presence of an object and sends information about the object to analysis process 642. Analysis process 642 identifies the object detected by number of motion detectors 618 and analyzes the data obtained by number of sensor components 616 such as, for example, number of images 650 from number of line scan cameras 620, ultraviolet light sources 630, and number of infrared sensors 636, as well as a number of images and measurements from laser metrology systems 628. Analysis process 642 may also identify whether or not the object detected is to be scanned by the different components of number of sensor components 616, scan priorities, if any, that exist for the object, and maintenance discrepancies found for the object. Analysis process 642 may generate scan results 652 to transmit to a maintenance unit and/or maintenance database, such as maintenance unit 406 and/or maintenance database 416 in FIG. 4.

User interface 644 allows for the input of data into sensor system 600 and/or analysis process 642, as well as displaying output from sensor system 600 and/or analysis process 642. User interface 644 may be, in one advantageous embodiment, presented on a display monitor, such as display 314 in FIG. 3.

In an advantageous embodiment, sensor system 600 may include a number of redundant sensors. As used herein, a number refers to one or more sensors. A number of sensors may be a heterogeneous and/or homogeneous number of sensors. Redundant sensors in these examples are sensors that may be used to compensate for the loss and/or inability of other sensors to obtain information needed to perform a scan of an object, such as an aircraft, for example. A redundant use of the number of sensors is governed by the intended use of each of the sensors and their degradation in certain dynamic conditions. For example, dynamic conditions may be terrestrial and weather conditions that affect sensors and their ability to contribute to an accurate scan of an object. Such conditions may include, without limitation, sun, clouds, artificial illumination, full moon light, new moon darkness, degree of sun brightness based on sun position due to season, shadows, fog, smoke, sand, dust, rain, snow, and the like.

The illustration of sensor system 600 in FIG. 6 is not meant to imply physical or architectural limitations on the manner in which different advantageous embodiments may be implemented. Other components in addition or in place of the ones illustrated may be used. Some components may be unnecessary in some advantageous embodiments. For example, in some advantageous embodiments, analysis process 642 could be located remotely from sensor system 600 and accessed using communications unit 640.

Also, the blocks are presented to illustrate some functional components and combined and/or divided into different blocks when implemented in hardware and/or software. For example, in some advantageous embodiments, analysis process 642 could be integrated with communications unit 640.

Figure 7:
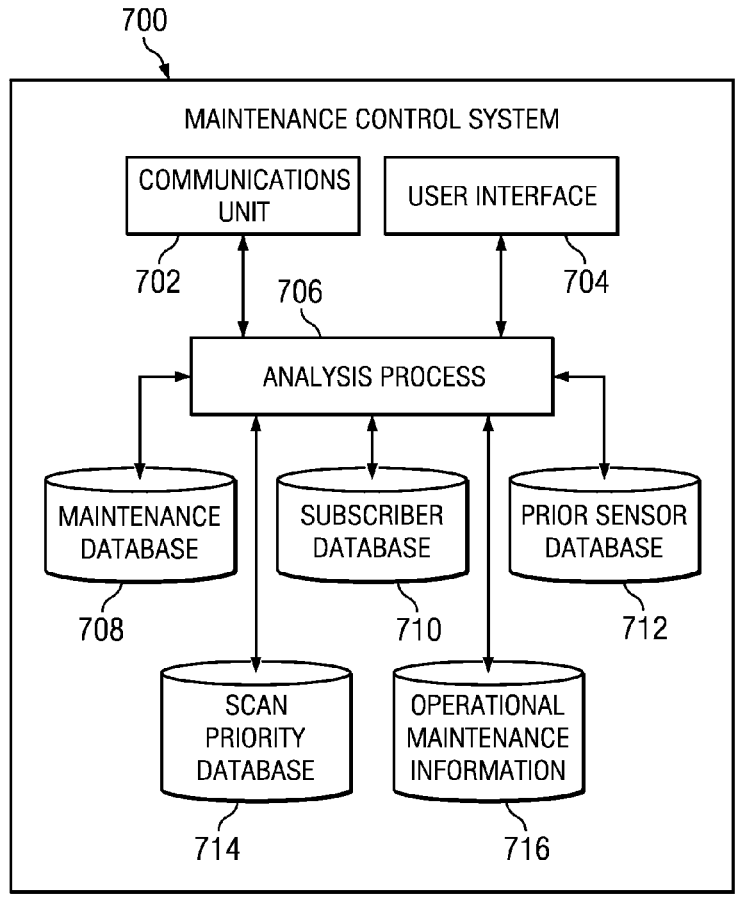
FIG. 7 is an illustration of a maintenance control system in accordance with an advantageous embodiment.

With reference now to FIG. 7, a diagram of a maintenance control system is depicted in accordance with an advantageous embodiment. Maintenance control system 700 may be implemented in a data processing system, such as data processing system 300 in FIG. 3. Maintenance control system 700 is an example of one implementation of maintenance control system 404 in FIG. 4.

Maintenance control system 700 includes communications unit 702, user interface 704, analysis process 706, maintenance database 708, subscriber database 710, prior sensor data 712, scan priority database 714, and operational maintenance information 716.

Communications unit 702, in these examples, provides for communications with other data processing systems or devices, such as sensor system 600 in FIG. 6 for example. In one advantageous embodiment, communications unit 702 may be a network interface card. Communications unit 702 may provide communications through the use of either or both physical and wireless communications links.

User interface 704 allows for the input of data into maintenance control system 700 and/or analysis process 706, as well as displaying output from maintenance control system 700 and/or analysis process 706. User interface 704 may be, in one advantageous embodiment, presented on a display monitor, such as display 314 in FIG. 3. In another advantageous embodiment, user interface 704 may also include peripherals such as, for example, a keyboard and mouse configured to interact with a monitor integrated with display 314 in FIG. 3.

In an advantageous embodiment, sensor system 600 in FIG. 6 detects a presence of an object and sends information about the object to analysis process 706. Analysis process 706 identifies the object detected by number of motion detectors 618 in FIG. 6 and analyzes the data obtained by number of sensor components 616 of sensor system 600 in FIG. 6. Analysis process 706 may also identify whether or not the object detected is to be scanned by a sensor system, such as sensor system 600 in FIG. 6, scan priorities, if any, that exist for the object, and maintenance discrepancies found for the object.

Maintenance database 708 contains maintenance planning data for a number of different models of an object as well as maintenance information for specific objects. For example, in one advantageous embodiment, maintenance database 708 contains maintenance planning data for a number of different models of an aircraft as well as maintenance information for a number of specific aircraft. In one advantageous embodiment, maintenance database 708 is a fleet-wide database used for tracking maintenance of aircraft at the macro and micro levels. This maintenance planning data describes what preventative maintenance must be performed to maintain airworthiness and federal compliance for a given aircraft. This information may include regulatory requirements and service bulletins.

Subscriber database 710 contains information about the customers that have subscribed to the service for scanning an object and identifying external anomalies. In one advantageous embodiment, subscriber database 710 may identify the tail numbers of aircraft that are owned by subscribers. Analysis process 706 may interact with subscriber database 710 to determine whether or not an object detected by a sensor system, such as sensor system 600 in FIG. 6, is an object that is a subscriber of the scanning service. If an object is not found within subscriber database 710, analysis process 706 may direct the sensor system not to perform a scan of the object. In another advantageous embodiment, analysis process 706 may receive the scan results, but may prevent the results from being processed if the object is not found within subscriber database 710.

Prior sensor data 712 contains information about prior scans of the object that is detected by a sensor system. Prior sensor data 712 may be used to detect reoccurring anomalies, or for trend monitoring for a particular object or type of object.

Scan priority database 714 contains a hierarchy of anomaly priorities for a sensor system to address. In an advantageous embodiment, scan priority database 714 may rank sections of an object, or particular anomalies that are to be sought out during a scan in order of priority. Priority may depend, in part, upon information obtained from operational maintenance information 716. In an advantageous embodiment, scan priorities are based on datalink transmissions received in-flight from an aircraft, and maintenance anomalies identified from the datalink transmission are given first tier priority to scan after flight.

Operational maintenance information 716 contains maintenance information transmitted during operation of an object. In an advantageous embodiment, operational maintenance information 716 may be maintenance information transmitted during flight of an aircraft, such as potential stress due to a hard landing or severe storm in-flight, for example. Operational maintenance information 716 may be transmitted via a datalink, such as the Aircraft Communications Addressing and Reporting System (ACARS) for example.

Analysis process 706 interacts with maintenance database 708, subscriber database 710, prior sensor data 712, scan priority database 714, and operational maintenance information 716 to identify potential maintenance needs for an object and assign scan priorities to a sensor system, such as sensor system 600 in FIG. 6.

The illustration of maintenance control system 700 in FIG. 7 is not meant to imply physical or architectural limitations on the manner in which different advantageous embodiments may be implemented. Other components in addition or in place of the ones illustrated may be used. Some components may be unnecessary in some advantageous embodiments. For example, in some advantageous embodiments, analysis process 706 could be located remotely from maintenance control system, for example integrated in sensor system 600 in FIG. 6, and access databases within maintenance control system 700 using communications unit 702.

Also, the blocks are presented to illustrate some functional components and combined and/or divided into different blocks when implemented in hardware and/or software. For example, in some advantageous embodiments, maintenance database 708, subscriber database 710, prior sensor data 712, scan priority database 714, and operational maintenance information 716 may be located in a storage device, such as persistent storage 308 in FIG. 3, or distributed over many data processing systems. As another example, in some advantageous embodiments, scan priority database 714 may prioritize anomaly tiers without additional operational maintenance information.

Figure 8:
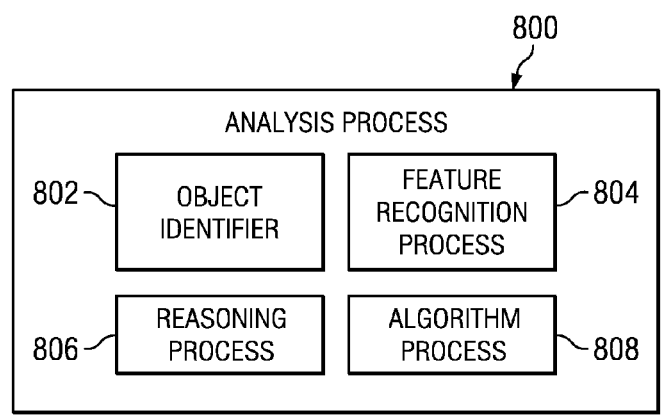
FIG. 8 is an illustration of an analysis process in accordance with an advantageous embodiment.

With reference now to FIG. 8, a diagram of an analysis process is depicted in accordance with an advantageous embodiment. Analysis process 800 may be implemented in a data processing system, such as data processing system 300 in FIG. 3. Analysis process 800 is an illustrative example of one implementation of analysis process 418 in FIG. 4.

Analysis process 800 includes object identifier 802, feature recognition process 804, reasoning process 806, and algorithm process 808. Object identifier 802 receives input from a sensor system, such as sensor system 600 in FIG. 6, when an object is detected. Object identifier 802 uses the information received, such as an image from a high definition camera, to detect an identifier of the object. For example, in an advantageous embodiment, a tail number of an aircraft may be an identifier detected from an image captured by a high definition camera. Object identifier 802 interacts with a subscriber database, such as subscriber database 710 in FIG. 7, to determine whether information about the object received from a sensor system should be processed, or whether a scan of the object by a sensor system should take place.

Feature recognition process 804 processes the information received from a sensor system and identifies what the information depicts. For example, if an ultraviolet light source and receptor detects a substance flowing from a surface, feature recognition process 804 identifies the substance as a fluid and the surface as the wing. In an illustrative example, a substance such as hydraulic fluid will illuminate when a specific wavelength of ultraviolet light shines on the surface of the hydraulic fluid. A sensor system, such as sensor system 600 in FIG. 6, may contain an ultraviolet light source and receptor, such as number of ultraviolet light sources 630 and ultraviolet receptor 632 in FIG. 6. When an aircraft passes by the sensor system, number of ultraviolet light sources 630 will shine light on the surface of the aircraft and ultraviolet receptor 632 will be programmed to detect the expected glow of the hydraulic fluid. Feature recognition process 804 recognizes the feature of a hydraulic fluid leak if illumination is detected by the sensor system. If no illumination is detected, analysis process 800 determines that there is no leak at the area of the surface scanned, such as a servicing point, for example. A servicing point may be, for example, refueling ports, single point refueling ports, wing refueling ports, hydraulic servicing ports, pneumatic servicing ports, and/or some other suitable servicing points.

Reasoning process 806 tags anomalies, or gripes, and keeps records of how anomalies are resolved. In an advantageous embodiment, over time, reasoning process 806 learns how particular anomalies are resolved and may diagnose anomalies detected. User input may be used to aid reasoning process 806 in learning how to correctly diagnose anomalies for future anomaly diagnosis. For example, in an advantageous embodiment, using the illustrative example of the hydraulic fluid leak above, in the absence of detected illumination, reasoning process 806 would determine that there is no leak. If illumination is detected, reasoning process 806 may send a command to the sensor system, such as sensor system 600 in FIG. 6, to capture an image for display to the maintenance crew, such as maintenance crew 422 in FIG. 4. The image may be captured using a camera, such as number of high definition cameras 622 in FIG. 6, for example. Reasoning process 806 may then determine that the illumination detected is a streak of fluid coming from a servicing point, for example, which may be an indication of a persistent leak. Reasoning process 806 may determine the amount of fluid present at the servicing point, and further determine that a small ring of fluid is residual fluid remaining from the last time hydraulic fluid was added to the reservoir, while a large streak of fluid is more indicative of a leak.

Reasoning process 806 determines the anomalies or anomalies present in order to generate a maintenance order. Reasoning process 806 receives user input as to how a number of anomalies are resolved and over time learns how specific anomalies are resolved, which allows reasoning process 806 to provide anomaly resolution diagnosis during subsequent processes.

Algorithm process 808 includes specific sets of instructions used by analysis process 800 to detect anomalies on an object. In one advantageous embodiment, algorithm process 808 uses algorithms that compare the data from the current scan of the object to known "as designed" data for the object. As designed data may be, for example, specific model data for an object. If the current scan of the object differs past a certain threshold from the "as designed" data for the object, algorithm process 808 will flag where the results are different as a possible anomaly. In another advantageous embodiment, algorithm process 808 uses algorithms that recognize certain patterns or shapes, and then compares the current scan of the object to the expected geometry of the object for the location of the object being scanned. For example, if the current scan is of a wing of an aircraft, algorithm process 808 may compare the current scan to the expected geometry for a wing location of the specific model and type of aircraft being scanned. If the shape of the location of the object in the current scan does not exist in the "as designed" data for the object, the shape at that location of the object will be flagged as a possible anomaly. For example, detecting an indention, such as a dent or hole, in what should be a flat area according to the as designed data would be a possible anomaly.

In an advantageous embodiment, reasoning process 806 takes the information processed by algorithm process 808 identifying an anomaly, such as a dent, for example, and recommends action in the form of a maintenance order to address the anomaly. Reasoning process 806 may process current anomalies detected by algorithm process 808 against reasoning process 806 knowledge of past anomalies and the actions taken to address past anomalies in order to determine the corrective action recommended in a maintenance order, for example.

The illustration of analysis process 800 in FIG. 8 is not meant to imply physical or architectural limitations on the manner in which different advantageous embodiments may be implemented. Other components in addition or in place of the ones illustrated may be used. Some components may be unnecessary in some advantageous embodiments. For example, in some advantageous embodiments, algorithm process 808 may contain additional algorithms or different algorithms than the algorithms mentioned above for illustrative purposes. Also, the blocks are presented to illustrate some functional components and combined and/or divided into different blocks when implemented in hardware and/or software. For example, in some advantageous embodiments, reasoning process 806 and algorithm process 808 may be integrated as one process.

Figure 9:
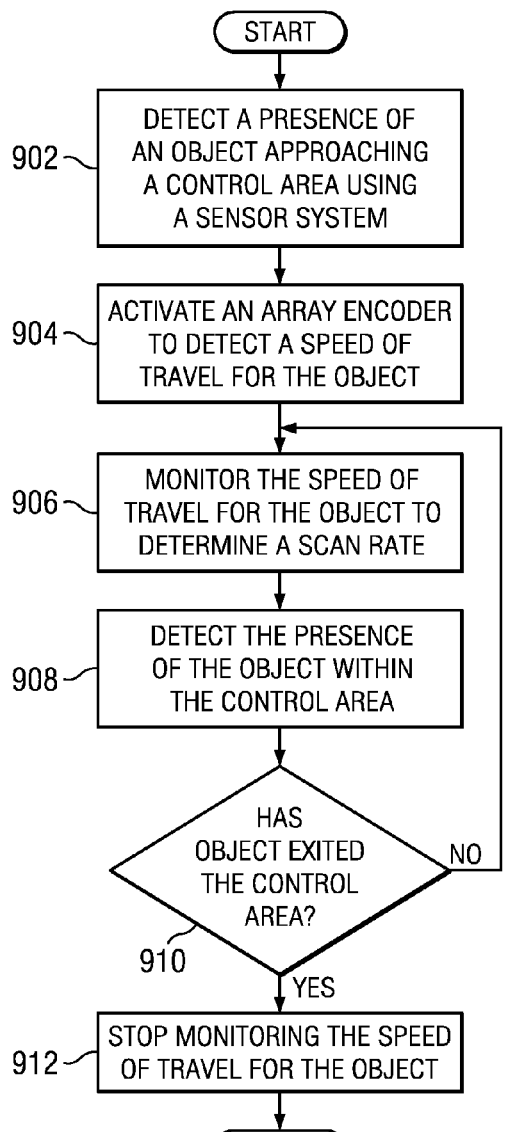
FIG. 9 is a flowchart illustrating a process for scanning an object in accordance with an advantageous embodiment.

With reference now to FIG. 9, a flowchart illustrating a process for scanning an object is depicted in accordance with an advantageous embodiment. The process in FIG. 9 may be implemented in a component such as, for example, sensor system 600 in FIG. 6.

The process begins by detecting a presence of an object approaching a control area using a sensor system (operation 902). The object may be, for example, an aircraft, such as aircraft 410 in FIG. 4, passing through a control area, such as control area 402 in FIG. 4. The object may be detected by a motion detector, such as number of motion detectors 618 in FIG. 6.

The process activates an array encoder to detect a speed of travel for the object (operation 904). The array encoder may be activated, or triggered, by detection of the object by a motion detector, for example. The process monitors the speed of travel for the object to identify a scan rate (operation 906). The scan rate may be determined based on the speed of travel for an object, which may vary as the speed of travel varies.

The process then detects the presence of the object within the control area (operation 908). The process determines whether the object has exited the control area (operation 910). If a determination is made that the object has not exited the control area, the process returns to operation 906, continually monitoring the speed of travel to update the scan rate as necessary as long as the object is within the control area.

If a determination is made that the object has exited the control area, the process stops monitoring the speed of travel for the object (operation 912), with the process terminating thereafter.

Figure 10:
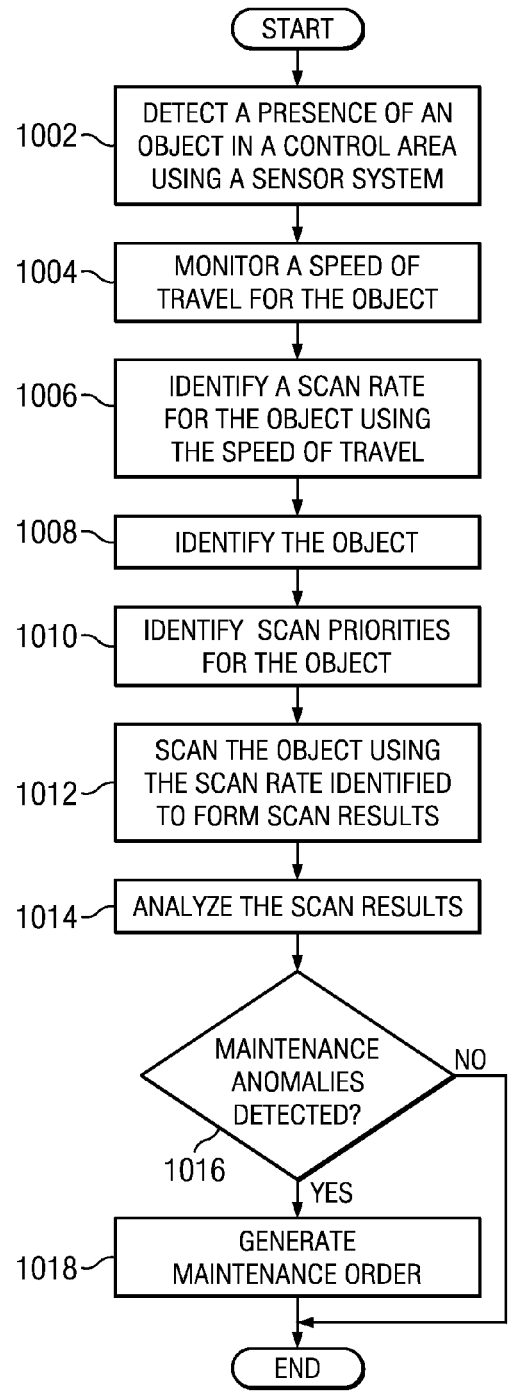
FIG. 10 is a flowchart illustrating a process for identifying maintenance anomalies in accordance with an advantageous embodiment.

With reference now to FIG. 10, a flowchart illustrating a process for identifying maintenance anomalies is depicted in accordance with an advantageous embodiment. The process in FIG. 10 may be implemented in a component such as, for example, sensor system 600 in FIG. 6.

The process begins by detecting a presence of an object in a control area using a sensor system (operation 1002). The object may be, for example, an aircraft, such as aircraft 410 in FIG. 4, moving through a control area, such as control area 402 in FIG. 4. The object may be detected by a motion detector, such as number of motion detectors 618 in FIG. 6. The process monitors the speed of travel for the object (operation 1004) using an array encoder, such as number of array encoders 626 in FIG. 6. The process identifies a scan rate for the object using the speed of travel (operation 1006).

The process identifies the object (operation 1008) using an object identifier, such as object identifier 802 in analysis process 800 of FIG. 8. The process then identifies scan priorities for the aircraft (operation 1010) using an analysis process, such as analysis process 646 in FIG. 6 and/or analysis process 800 in FIG. 8.

Next, the process scans the object using the scan rate identified to form scan results (operation 1012). The process analyzes the scan results (operation 1014) using an analysis process, such as analysis process 800 in FIG. 8. Then the process determines whether maintenance anomalies are detected (operation 1016). If no maintenance anomalies are detected, the process terminates.

If maintenance anomalies are detected, the process generates a maintenance order (operation 1018), with the process terminating thereafter. A maintenance anomaly is any type of anomaly that requires maintenance. The anomaly may be inside the object, on an exterior surface of the object, on an interior surface of the object, within a structure of the object, and/or any other suitable area of the object.

The flowcharts and block diagrams in the different depicted embodiments illustrate the architecture, functionality, and operation of some possible implementations of apparatus and methods in different advantageous embodiments. In this regard, each block in the flowchart or block diagrams may represent a module, segment, function, and/or a portion of an operation or step. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The different advantageous embodiments recognize and take into account that currently used systems for conducting post-flight maintenance lose the time from when an aircraft lands until it reaches the ramp from the runway, which increases the potential turn around time due to maintenance requirements that may not be identified until the aircraft has finished taxiing. The different advantageous embodiments recognize that initial maintenance inspection time is lost while an aircraft is taxiing.

The different advantageous embodiments recognize and take into account that currently used systems for identifying external maintenance anomalies for an aircraft, for example, rely upon human inspection at the airport gate or maintenance area. The different advantageous embodiments recognize that the locations at which inspection for external maintenance anomalies can take place is limited. The different advantageous embodiments also recognize that currently used systems may cope with this problem by utilizing maintenance datalinks, which have the ability to detect some structural health issues but lack any ability to autonomously detect latent surface anomalies, such as cracks or dents for example.

The different advantageous embodiments also recognize and take into account that maintenance datalinks are expensive and have bandwidth limitations that significantly restrict the amount of information that can be transmitted. The different advantageous embodiments recognize that this leads to many companies choosing not to use maintenance datalinks at all, and relying solely on inspections that take place after the aircraft has finished taxiing.

Thus, different advantageous embodiments provide a method and apparatus for quicker troubleshooting information for an aircraft anomaly, and regularly occurring, repetitive inspections that may detect anomalies that have indications outside of the human visual spectrum. Maintenance crews can address anomalies more efficiently without lost time for inspection, and focus on conducting the required maintenance. The different advantageous embodiments provide a system capable of automatically acquiring optical imagery of a vehicle's surfaces in one or more optical spectrums using the speed of the vehicle to determine the scan rate for a sensor array system.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk—read only memory (CD-ROM), compact disk—read/write (CD-R/W) and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation to keyboards, touch screen displays, and pointing devices.

Different communications adapters may also be coupled to the system to enable the data processing system to become coupled to other data processing systems or remote printers or storage devices through intervening private or public networks. Non-limiting examples are modems and network adapters are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art. For example, although the different advantageous embodiments have been described with respect to aircraft, other advantageous embodiments may be applied to other types of objects. For example, without limitation, other advantageous embodiments may be applied to a mobile platform, a stationary platform, a land-based structure, an aquatic-based structure, a space-based structure and/or some other suitable object. More specifically, the different advantageous embodiments may be applied to, for example, without limitation, a submarine, a bus, a personnel carrier, tank, a train, an automobile, a spacecraft, a space station, a satellite, a surface ship, and/or some other suitable object.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying anomalies for an aircraft, the method comprising:
    detecting a presence of the aircraft in a control area via monitoring, using a sensor system, the aircraft characterized by a first side, a second side, and a bottom;
    responsive to the sensor system detecting the presence of the aircraft in the control area, identifying, using a number of array encoders, a speed of travel for the aircraft;
    determining a scan rate for the aircraft using the speed of travel, wherein the scan rate is a number of electrical signal pulses sent to a number of cameras resulting in the number of cameras taking an exposure of at least a portion of the aircraft on each of the number of electrical signal pulses;
    identifying, using a maintenance control system comprising a computer comprising an analysis process comprising an object identifier, the aircraft;
    responsive to identifying the aircraft, identifying, using the analysis process and a scan priority database comprising a hierarchy of anomaly priorities, a number of scan priorities for the aircraft on the ground after a flight, wherein the number of scan priorities ranks different sections of the aircraft to be sought out during a scan based on information comprising operational maintenance information about the aircraft;
    determining whether the analysis process received a datalink communication, identifying an anomaly with a section of the aircraft, from the aircraft during the flight;
    assigning a first priority to the anomaly identified in the datalink communication, and responsive to receiving identification of multiple anomalies, identifying prioritization of the multiple anomalies received in the datalink communication based upon a hierarchy of anomaly priorities within a scan priority database communicating with the analysis process;
    identifying prior scan results for the aircraft;
    determining, using the analysis process and the prior scan results, whether an anomaly trend exists;
    responsive to a determination that the anomaly trend exists, assigning a second priority to the anomaly trend;
    determining, using a designated use for each sensor in the sensor system and a potential for degradation of each sensor influenced by dynamic conditions comprising: a cloud coverage, an artificial illumination, a full moon light, a new moon darkness, a degree of sun brightness based on sun position due to season, a shadow, fog, smoke, sand, dust, rain, and snow, a number of redundant sensors in the sensor system used in scanning the aircraft;
    responsive to identifying the number of scan priorities for the aircraft, scanning the aircraft, using the scan rate and a number of sensor components in an array in accordance with the number of scan priorities, the array including at least a horizontal array of sensors directed at the bottom of the aircraft and an angled array of sensors directed at the first side of the aircraft; and
    responsive to scanning the aircraft, using the analysis process for forming scan results and determining whether a number of maintenance anomalies is present among a set of locations for the aircraft, the set comprising: inside the aircraft, on an exterior surface of the aircraft, on an interior surface of the aircraft, and within a structure comprising the aircraft;
    responsive to determining that the number of maintenance anomalies is present for the aircraft, generating a maintenance action to address the number of maintenance anomalies detected, transmitting the maintenance action to a maintenance unit, and executing the maintenance action on the aircraft.

2. The method of claim 1 further comprising:
    the number of cameras comprising a camera comprising a line scan technology; and
    transmitting the maintenance action to at least one of: a maintenance unit, and a maintenance database.

3. The method of claim 1, further comprising housing the number of sensor components providing the scan results for the aircraft within a weather resistant housing comprising a number of heating elements keeping each sensor, in the number of sensor components, at a desired operating temperature for each sensor.

4. The method of claim 1 further comprising:
    responsive to a number of maintenance inconsistencies present for the aircraft, performing maintenance on the aircraft.

5. The method of claim 1 further comprising:
    transmitting the scan results to the maintenance control system, wherein the maintenance control system analyzes the scan results and determines whether the number of maintenance anomalies is present for the aircraft.

6. The method of claim 1 further comprising:
    identifying a tail number of the aircraft using the object identifier; and
    determining, based upon an object identifier interaction with a subscriber database, whether information received from the sensor system should be processed.

7. The method of claim 1, further comprising a horizontal array viewing a bottom surface of a wing of the aircraft and the angled array viewing an upper surface of the wing.

8. The method of claim 1, further comprising the number of sensor components comprising: an array encoder, a laser metrology system, a number of ultraviolet light sources, a number of ultraviolet receptors, and a number of infrared sensors.

9. A method for identifying a scan rate for a scan of the object, the object having a first side, a second side, and a bottom, the method comprising:

detecting a presence of the object approaching a control area using a sensor system, the control area comprising an area that overlies a horizontal sensor array and is adjacent to a vertical sensor array and an angled sensor array, the vertical sensor array being at an angle of 90 degrees relative to the horizontal sensor array, and the angled sensor array being at an angle other than 90 degrees relative to the horizontal sensor array, the angled sensor array comprising a number of sensor components comprising: an array encoder, a laser metrology system, a number of ultraviolet light sources, a number of ultraviolet receptors, a camera comprising a line scan technology, and a number of infrared sensors;

determining whether a maintenance control system comprising a computer comprising an analysis process received a datalink communication, identifying an anomaly with a section of the object, from an aircraft during a flight;

assigning a first priority to the anomaly identified in the datalink communication, and responsive to receiving identification of multiple anomalies, identifying prioritization of the multiple anomalies received in the datalink communication based upon a hierarchy of anomaly priorities within a scan priority database communicating with the analysis process;

identifying prior scan results for the object;

determining, using the analysis process and the prior scan results, whether an anomaly trend exists;

assigning, responsive to a determination that the anomaly trend exists, a second priority to the anomaly trend;

identifying preventative maintenance requirements; and assigning a third priority to preventative maintenance requirements;

determining, using a designated use for each sensor in the sensor system and a potential for degradation of each sensor influenced by dynamic conditions comprising: a cloud coverage, an artificial illumination, a full moon light, a new moon darkness, a degree of sun brightness based on sun position due to season, a shadow, fog, smoke, sand, dust, rain, and snow, a number of redundant sensors in the sensor system used in scanning the aircraft;

detecting a speed of travel for the object via activating the array encoder; and monitoring the speed of travel for the object to determine the scan rate for the object, wherein the scan rate is a number of electrical signal pulses sent to a number of cameras to cause the number of cameras to take an exposure of the object on each of the number of electrical signal pulses, and generating scan results from the number of sensor components;

responsive to the scan results, generating the maintenance action to address maintenance anomalies detected, transmitting the maintenance action to a maintenance unit, and executing the maintenance action on the object.

10. The method of claim 7 further comprising:

detecting the presence of the object within the control area;

determining whether the object has exited the control area; and responsive to a determination that the object has not exited the control area, monitoring the speed of travel for the object.

11. The method of claim 10 further comprising:

responsive to determining that the object has exited the control area, stopping monitoring of the speed of travel for the object.

12. The method of claim 9, wherein the array encoder is activated by detection of the object using a motion detector.

13. The method of claim 7 further comprising:

continually monitoring the speed of travel for the object to update the scan rate while the object is within the control area.

14. The method of claim 9, wherein the object is an aircraft configured to transmit operation maintenance information, to the analysis process, for identifying scan priorities.

15. The method of claim 9, further comprising housing the number of sensor components within a weather resistant housing comprising a number of heating elements keeping each sensor array at a desired operating temperature for each sensor.

16. An apparatus for identifying anomalies for an object, the object comprising a first side, a second side, and a bottom, the apparatus comprising:

a sensor system configured:

to detect a presence of the object in a control area;

comprising a horizontal sensor array adjacent to a vertical sensor array and an angled sensor array, the vertical sensor array being at an angle of 90 degrees relative to the horizontal sensor array, and the angled sensor array being at an angle other than 90 degrees relative to the horizontal sensor array, such that the angled sensor array comprises a number of sensor components that comprises: an array encoder, a laser metrology system, a number of ultraviolet light sources, a number of ultraviolet receptors, a camera comprising a line scan technology, and a number of infrared sensors;

to identify a speed of travel for the object; and to determine, using the speed of travel, a scan rate for the sensor to scan the object to generate scan results, wherein the scan rate is a number of electrical signal pulses sent to a number of cameras to cause the number of cameras to take an exposure of the object on each of the number of electrical signal pulses and wherein the scan results are generated from a number of sensor components in accordance with a number of scan priorities;

a maintenance control system that comprises a computer that comprises a scan priority database that comprises a hierarchy of anomaly priorities, such that the computer comprises an analysis process configured to:

determine whether a maintenance control system that comprises the computer receives a datalink communication, that identifies an anomaly with a section of the object, from an aircraft during a flight;

assign a first priority to the anomaly identified in the datalink communication, and responsive to receipt of identification of multiple anomalies, identify prioritization of the multiple anomalies received in the datalink communication based upon a hierarchy of anomaly priorities within a scan priority database that communicates with the analysis process;
identify prior scan results for the aircraft;
determine, based upon the analysis process and the prior scan results, whether an anomaly trend exists;
responsive to a determination that the anomaly trend exists, assign a second priority to the anomaly trend;
determine, based upon a designated use for each sensor in the sensor system and a potential for degradation of each sensor influenced by dynamic conditions that comprise: a cloud coverage, an artificial illumination, a full moon light, a new moon darkness, a degree of sun brightness based on sun position due to season, a shadow, fog, smoke, sand, dust, rain, and snow, a number of redundant sensors in the sensor system used in scanning the aircraft;
direct a prioritized scan of the object;
analyze a result of the prioritized scan; and
determine, based upon the result, a number of maintenance anomalies for the object;
direct actions based upon the number of maintenance anomalies, such that a maintenance unit executes the actions on the object.

17. The apparatus of claim 16, wherein the analysis process is further configured to;
identify a preventative maintenance requirement for the object; and
assign a third priority to the preventative maintenance requirement for the object.

18. The apparatus of claim 16, wherein the sensor system further comprises:
a number of sensor arrays that comprise a number of array locations, wherein the number of sensor arrays provide a number of scan angles for the sensor system associated with the number of sensor arrays.

19. The apparatus of claim 18 further comprising:
the number of sensor components being located at the number of array locations.

* * * * *